(12) United States Patent
Kortenbach

(10) Patent No.: US 9,433,410 B2
(45) Date of Patent: *Sep. 6, 2016

(54) TISSUE FASTENING DEVICES AND RELATED INSERTION TOOLS AND METHODS

(71) Applicant: Boston Scientific Scimed, Inc., Maple Grove, MN (US)

(72) Inventor: Juergen A. Kortenbach, Miami Springs, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 157 days.

This patent is subject to a terminal disclaimer.

(21) Appl. No.: 14/146,355

(22) Filed: Jan. 2, 2014

(65) Prior Publication Data

US 2014/0121683 A1    May 1, 2014

Related U.S. Application Data

(63) Continuation of application No. 12/880,868, filed on Sep. 13, 2010, now Pat. No. 8,647,351, which is a continuation of application No. 11/488,191, filed on Jul. 18, 2006, now Pat. No. 7,811,295, which is a continuation of application No. 10/138,028, filed on May 1, 2002, now Pat. No. 7,077,850.

(51) Int. Cl.
*A61B 17/10* (2006.01)
*A61B 17/064* (2006.01)
*A61B 17/068* (2006.01)
*A61B 17/00* (2006.01)

(52) U.S. Cl.
CPC ........... *A61B 17/064* (2013.01); *A61B 17/068* (2013.01); *A61B 2017/00827* (2013.01); *A61B 2017/0649* (2013.01)

(58) Field of Classification Search
CPC .............. A61B 2017/0082; A61B 2017/0649; A61B 2017/0647; A61B 17/064
See application file for complete search history.

(56) References Cited

U.S. PATENT DOCUMENTS

| 5,207,695 A | 5/1993 | Trout, III |
| 5,222,976 A | 6/1993 | Yoon |
| 5,259,394 A | 11/1993 | Bens |
| 5,330,503 A | 7/1994 | Yoon |
| 5,499,990 A | 3/1996 | Schülken et al. |
| 5,582,616 A | 12/1996 | Bolduc et al. |
| 5,830,221 A * | 11/1998 | Stein et al. ................... 606/157 |

(Continued)

FOREIGN PATENT DOCUMENTS

WO    WO 00/69345    11/2000

OTHER PUBLICATIONS

International Search Report for PCT/US0311490, mailed Oct. 9, 2003.

*Primary Examiner* — Gregory Anderson
*Assistant Examiner* — Christina Lauer
(74) *Attorney, Agent, or Firm* — Bookoff McAndrews, PLLC

(57) ABSTRACT

The invention in certain aspects relates to a one-piece coil-shaped surgical fastener for fastening tissue segments, especially suitable for fastening segments of the lower esophageal sphincter and fundus in an endoscopic procedure for the treatment of GERD. The invention also relates to related methods and devices for insertion of such a fastener, especially along a juncture of the surfaces of such tissue segments.

20 Claims, 8 Drawing Sheets

(56) References Cited

U.S. PATENT DOCUMENTS

| | | | |
|---|---|---|---|
| 5,865,791 A | 2/1999 | Whayne et al. | |
| 5,944,750 A | 8/1999 | Tanner et al. | |
| 5,957,940 A | 9/1999 | Tanner et al. | |
| 5,964,772 A | 10/1999 | Bolduc et al. | |
| 5,972,023 A | 10/1999 | Tanner et al. | |
| 6,086,600 A | 7/2000 | Kortenbach | |
| 6,159,146 A | 12/2000 | El Gazayerli | |
| 6,248,118 B1 | 6/2001 | Tanner et al. | |
| 6,371,919 B1 | 4/2002 | Tanner et al. | |
| 6,409,757 B1 | 6/2002 | Trout, III et al. | |
| 6,478,791 B1 | 11/2002 | Carter et al. | |
| 6,520,974 B2 | 2/2003 | Tanner et al. | |
| 6,558,400 B2 | 5/2003 | Deem et al. | |
| 6,607,555 B2 | 8/2003 | Patterson et al. | |
| 6,635,066 B2 | 10/2003 | Tanner et al. | |
| 6,648,912 B2 | 11/2003 | Trout, III et al. | |
| 6,706,047 B2 | 3/2004 | Tanner et al. | |
| 6,855,159 B1 | 2/2005 | Tanner et al. | |
| 7,077,850 B2 | 7/2006 | Kortenbach | |
| 7,811,295 B2 | 10/2010 | Kortenbach | |
| 2002/0040226 A1* | 4/2002 | Laufer et al. | 606/153 |
| 2002/0082621 A1* | 6/2002 | Schurr | A61B 17/0643 606/151 |

\* cited by examiner

TISSUE FASTENING DEVICES AND RELATED INSERTION TOOLS AND METHODS

This is a continuation of U.S. application Ser. No. 12/880,868, filed Sep. 13, 2010, now U.S. Pat. No. 8,647,351, which is a continuation of U.S. application Ser. No. 11/488,191, filed Jul. 18, 2006, now U.S. Pat. No. 7,811,295, which is a continuation of U.S. application Ser. No. 10/138,028, filed May 1, 2002, now U.S. Pat. No. 7,077,850, all of which are incorporated by reference herein in their entireties.

FIELD OF THE INVENTION

The present invention relates to surgical fasteners and, particularly, to tissue fasteners. Still more particularly, the present invention relates to tissue fasteners especially for use in a GERD fundoplication procedure.

BACKGROUND OF THE INVENTION

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus into the stomach. This pressure essentially closes the esophagus so that contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, typically resulting in occasional bouts of heartburn.

The physical interaction occurring between the gastric fundus and the esophagus also prevents gastroesophageal reflux. The gastric fundus is a lobe of the stomach situated at the top of the stomach proximal to the esophagus. In healthy individuals, the fundus presses against the opening of the esophagus when the stomach is full of food and/or gas. This effectively closes off the esophageal opening to the stomach and helps to prevent acid reflux back into the esophagus.

In individuals with GERD, the LES functions abnormally, either due to an increase in transient LES relaxations, decrease in length of the esophagus, decreased muscle tone of the LES during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not cure the disease completely.

A surgical procedure, known generally as fundoplication, has been developed to prevent acid reflux in patients whose normal LES functioning has been impaired, either as a result of GERD or otherwise. Fundoplication involves bringing the fundus into closer proximity to the esophagus to help close off the esophageal opening into the stomach. In Nissen Fundoplication, a particular type of the fundoplication procedure, the fundus is pulled up and around the esophagus and then sutured to itself and the esophagus such that it completely encircles the esophagus. Traditionally, this procedure has been performed as an open surgery, but has recently enjoyed success as a laparoscopic procedure, as discussed in McKeman, J. B., Champion, J. K., "Laparoscopic antireflex surgery," *American Surgeon*, Vol. 61, pp. 530-536, (1995).

As with any open surgery, complications can occur as a result of infection, blood loss or from the use of anesthesia. Further, the relatively large incisions necessary in the performance of open surgery require extended recovery times for the incision to heal. Though laparoscopic surgical procedures reduce these negative effects by using relatively small devices at a relatively small incision site in the abdominal wall, there still exists an increased risk of infection due to the incision. The location of the incision in the abdominal wall presents a risk of other negative effects, such as sepsis, which can be caused by leakage of septic fluid contained in the stomach.

Other surgical procedures specifically address the LES. These procedures attempt to prevent reflux by thickening the LES region and reducing the diameter of the esophageal opening to the stomach, i.e., tighten the LES region. However, existing procedures are lengthy and difficult to perform.

SUMMARY OF THE INVENTION

The present invention includes tissue fasteners and related methods for an endoluminal tissue fastening procedure, especially suitable for the treatment of GERD. To attain the advantages and in accordance with the purpose of the invention, as embodied and broadly described herein, the invention includes a one-piece surgical fastener for fastening tissue segments. The fastener includes a coil-shaped portion having a proximal end and a distal end, a sharp tip at the distal end of the coil-shaped portion, and a substantially straight portion extending along the proximal end of the coil-shaped portion and substantially perpendicular to an axis of the coil-shaped portion.

According to other aspects, the invention includes a device for fastening a first segment of lower esophageal sphincter tissue to a second segment of fundus tissue. The device includes a one-piece tissue fastener having a coil-shaped portion and an elongate body configured for insertion into the esophagus. The elongate body has a proximal end and a distal end portion, and a passageway extending from the proximal end to the distal end portion to allow the passage of the fastener through the elongate body. The device also includes an element connected to and pivoting from the distal end of the elongate body. The element has an extended position at an angle to an axis of the elongate body and a retracted position substantially along an axis of the elongate body to hold the first and second tissue segments between the element and the distal end portion of the elongate body. The device further includes a tissue fastener advancer located in the passageway for advancing the tissue fastener in the passageway to the distal end portion of the elongate body and into the first and second tissue segments.

According to still further aspects, the invention includes a device for inserting a coil-shaped tissue fastener into body tissue segments. The device includes a housing having a proximal end, a distal end portion, a body portion extending therebetween, and a passageway extending from the proximal end through the body portion and terminating at the distal end portion allowing the passage of fasteners through the housing. The device also includes an arm pivotally attached to the housing at the distal end portion and configured to hold the tissue segments to be fastened between the arm and the distal end portion of the housing. The device further includes means for advancing the fastener through the passageway and into the tissue segments held between the arm and the distal end portion.

According to even further aspects, the invention includes a method of fastening a first segment of lower esophageal sphincter tissue to a second segment of fundus tissue. The method includes the steps of holding a first surface of the first tissue segment to a second surface of the second tissue segment; and inserting a coil-shaped fastener along a juncture of the first and second surfaces.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments the invention, examples of which are illustrated in the accompanying drawings. Wherever possible, the same reference numbers will be used throughout the drawings to refer to the same or like parts.

A newly developed form of fundoplication, referred to as endoscopic fundoplication, is an endoluminal procedure in which the fundus wall is folded back onto the esophagus wall. The tissue fold formed between the esophagus and the fundus then is secured. Endoscopic fundoplication is intended to be performed as an endoluminal procedure in which insertion of required medical instruments occurs through the esophagus. Such a procedure has the benefits of being less invasive, quicker, and less expensive as compared to previous techniques.

The present invention is directed to fasteners and methods especially suitable to fasten tissue in an endoscopic fundoplication procedure. According to embodiments of the present invention, the tissue fastener is in the form of a one-piece coil, and the insertion device is adapted to receive and insert the one-piece coil fasteners. In embodiments of the invention, the insertion device is adapted to helically wind the coil fastener through both the tissue layers and along an axis substantially parallel to the contact surfaces of the tissue layers. The insertion device according to the present invention may be used in connection with an endoscope for viewing the operation site, or other suitable endoscopic devices.

Figure 1:
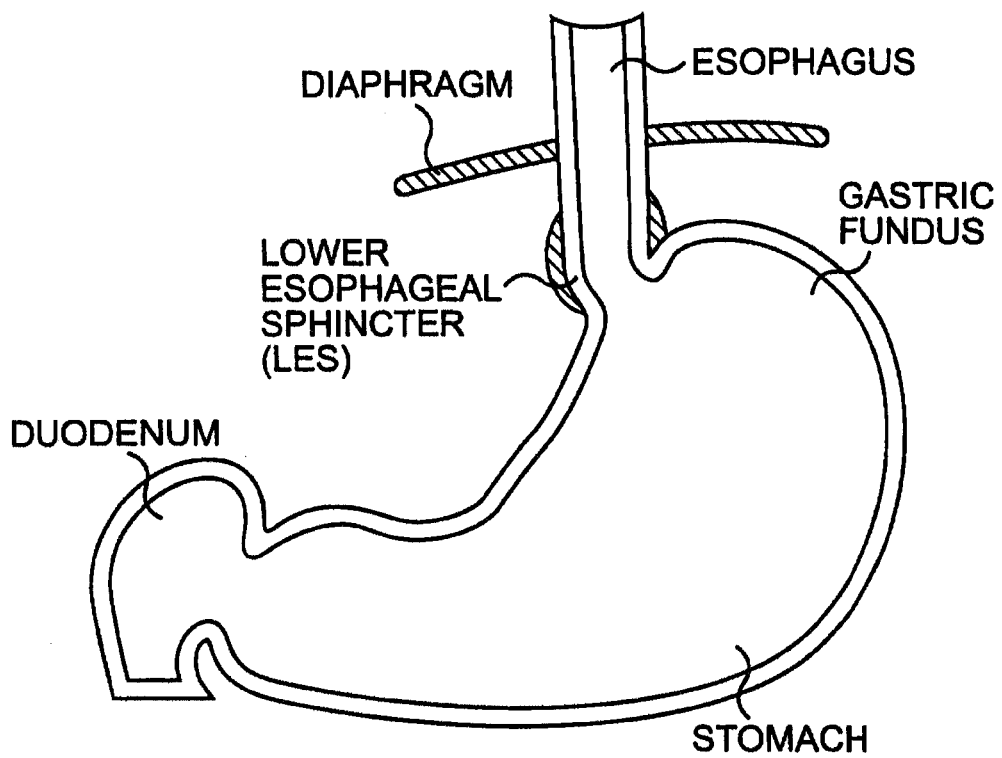
FIG. 1 is a cross-sectional view of the gastrointestinal tract from a mid-point of the esophagus to a point near the beginning of the duodenum.
Figure 2:
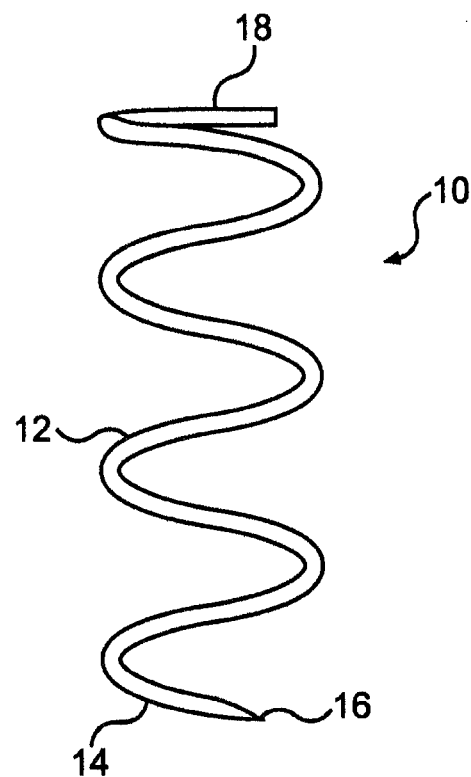
FIGS. 2 and 2(a) respectively are side and end views of a tissue fastener, according to an embodiment of the present invention.
Figure 2A:
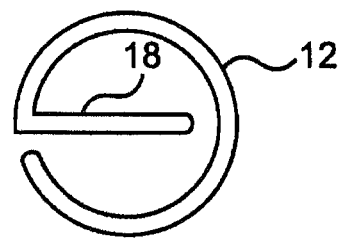

FIGS. 2 and 2(a) show a fastener 10 according to an embodiment of the present invention. Fastener 10 is shown as a helical coil 12. Coil 12 has a leading end 14, preferably terminating in a point 16 for piercing the tissue segments to be joined and easing the introduction of fastener 10 into the tissue segments to be joined. The other end of coil 12 terminates in a portion 18 bent along the diameter of coil 12. Portion 18 is substantially straight and extends along the end of coil 12 and substantially perpendicular to an axis of coil 12.

The size (including diameter and length), pitch, and composition of coil 12 may vary according to the particular application of fastener 10, including, for example, the length and width of the tissue segments to be fastened. Examples of coil dimensions include a diameter of about ⅛" to ¾", and preferably about ⅜" diameter, and a length of about 5 mm to 12 mm, and preferably about 6 mm in diameter. Coil 12 may be constructed from any biocompatible material having sufficient properties, including appropriate rigidity, to retain two segments of tissue together. Suitable biocompatible materials include stainless steel (316 SS), nitinol, titanium, shape memory polymers such as polynorbene, polyethylene, PLLA, PGA, polyurethane, and PTFE, ceramics, and compositions of materials such as a metal and a polymer or a filled polymer. In addition, coil 12 could be constructed from any suitable bioabsorbable materials. If coil 12 is made of a bioabsorbable material, coil 12 would fasten the tissue segments together for an amount of time sufficient for the segments to grow into one another.

Figure 3:
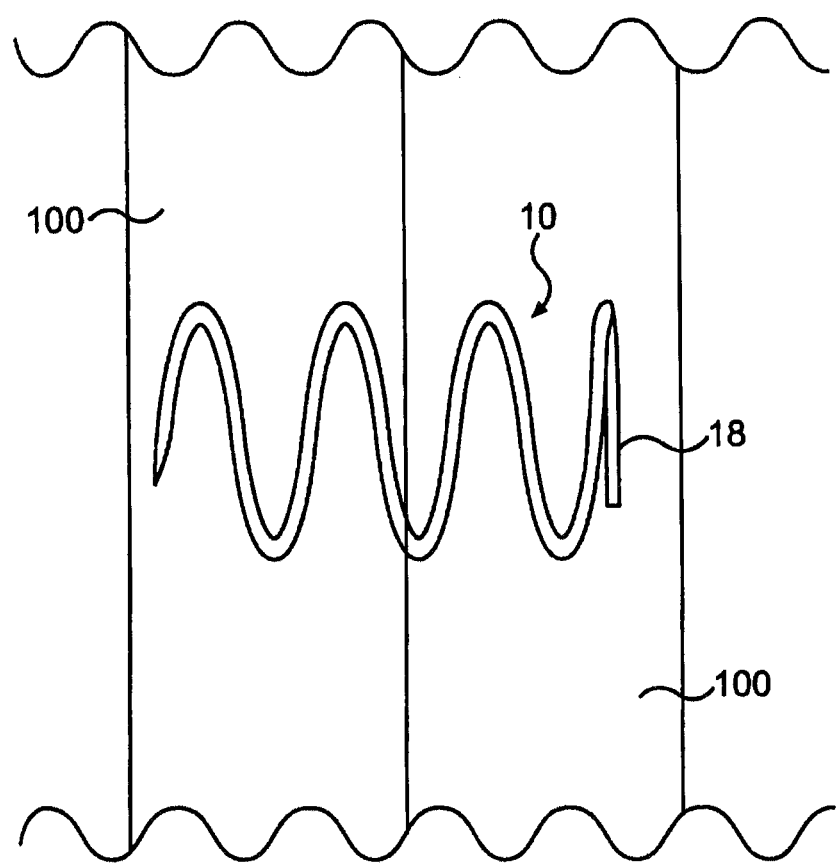
FIG. 3 is a sectional side view of the fastener of FIG. 2 inserted consecutively through tissue segments, according to an embodiment of the present invention.
Figure 4:
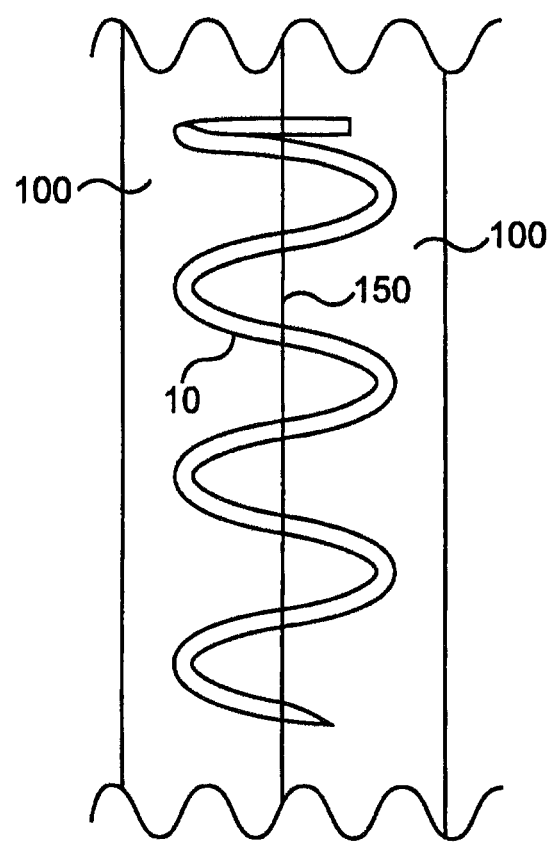
FIG. 4 is a sectional side view of the fastener of FIG. 2 inserted along the juncture of tissue segments, according to an embodiment of the present invention.

Fastener 10 may be wound helically into the tissue layers to be joined. Fastener 10 may be wound consecutively through each tissue layer 100, as shown in FIG. 3. In a preferred arrangement, fastener 10 is wound simultaneously through both tissue layers 100 along a juncture 150 of tissue layers 100, as shown in FIG. 4. In that case, fastener 10 extends along an axis substantially parallel to juncture 150. By inserting the fastener along the juncture of the tissue layers, the size of the fastener need not be dependent on the thickness of the tissue layers. Because the fastener does not have to pass through the thickness of the tissue layers but rather passes along the longitudinal axis of the juncture of the tissue layers, fastener 10 does not have to be of length to pass from one tissue layer to the adjoining tissue layer. As a result, the same fastener may be used on tissue layers of varying thickness.

The fastener also provides numerous other benefits by running along the length of the tissue juncture. As examples, the fastener provides a relatively close and tight retention of the tissue segments, and the fastener reduces the total number of fasteners needed for a procedure. More specifically, one fastener of length x may be used to secure a length x of fundus to the esophagus.

The present invention also provides a device for insertion of fasteners described above. As will be described, the fastener insertion devices according to embodiments of the invention can easily reach internal body sites, including the esophagus and stomach, can be used with fasteners of varying length and size, and can be used with multiple fasteners at one time.

Figure 5:
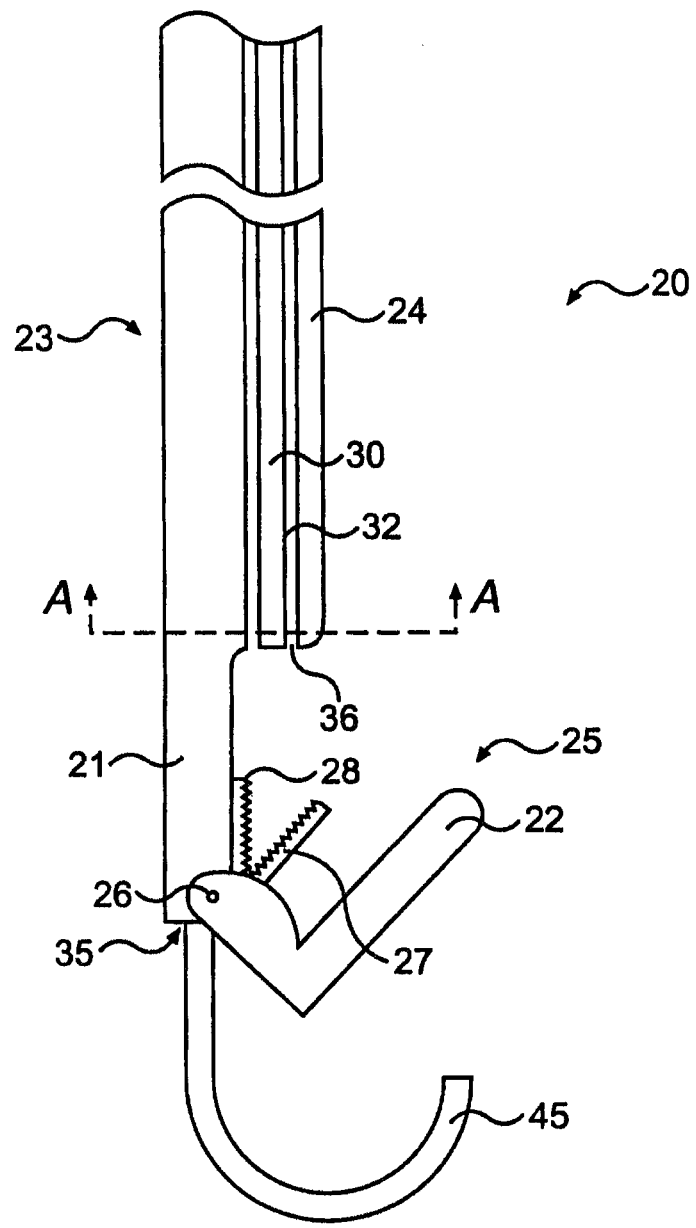
FIG. 5 is a side sectional view of a tissue fastener insertion device, according to an embodiment of the present invention.

FIG. 5 shows an embodiment of a tissue fastener insertion device 20 according to the present invention. Device 20 is used to insert one or more fasteners 10 into tissue segments to be joined. Insertion device 20 includes an elongate member 23 having a main body portion 24 and a distal end portion 21. Elongate member 23 has a sufficient length so that member 23 extends from a proximal end (not shown) that remains outside of a patient during an endoluminal fundoplication procedure, through the esophagus, and to distal end portion 21 in a stomach of the patient.

A jaw assembly 25 articulates relative to distal end portion 21 at pivot 26. A pin may be inserted within holes of jaw assembly 25 and end portion 21 to attach assembly 25 to end portion 21 and allow relative pivotal movement. Other suitable means for connecting jaw assembly 25 to end portion and permitting relative pivotal movement may be used.

Jaw assembly 25 includes a rotatable grasper 27 that rotates relative to a stationary grasper 28 to grasp the gastroesophageal junction. Graspers 27 and 28 may include teeth for effectively grasping the tissue. The teeth may be blunt or sharp depending on the type of tissue being grasped and the needs of the physician operating device 20. It is to be understood that grasper 28 alternatively may be pivotal. In addition, rather than graspers 27 and 28 being integral with device 20, an endoscopic grasping tool may be inserted through a lumen of device 20 to the operative site for grasping the gastroesophageal junction.

Jaw assembly 25 also includes a relatively large pivoting outer arm 22 to fold the fundus of the stomach onto the esophagus and retain the fundus in that position while a fastener is being inserted into the tissue fold.

The mechanism for actuation of jaw assembly 25, including graspers 27,28 and arm 22, may include any suitable mechanism known to those in the art of endoscopic medical devices. As examples only, actuation mechanisms that incorporate cables, vacuum, hydraulics, linkages, and/or cams may be used. Further examples of suitable actuation mechanisms for endoluminal procedures, and details of fastener insertion devices, include those shown and described in U.S. Pat. Nos. 6,113,609 and 6,086,600, the entire disclosures of which are incorporated by reference herein. In an alternate embodiment, the graspers are separate from the insertion device and jaw assembly. The graspers may be any medical device known in the art to grasp tissue including, but not limited to, graspers, forceps, and baskets. The device is delivered to the tissue through a channel of the insertion device or adjacent to the insertion device.

Figure 6:
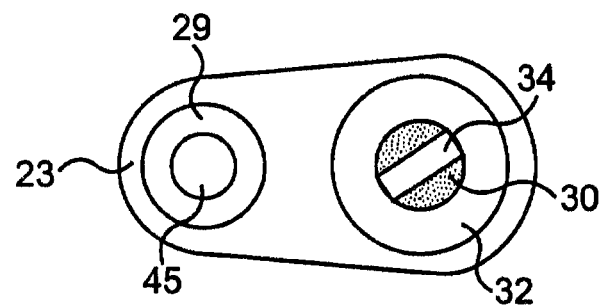
FIG. 6 is a cross-sectional view of the insertion device of FIG. 5 taken along line A-A.

As best shown in FIG. 6, insertion device 20 further includes a first passageway 29 for accommodating one or more endoscopic devices desired to be used in the procedure. Passageway 29 extends from a proximal end of device 20, through portion 24, and terminates at an opening 35 at distal end portion 21. As an example, an endoscope 45 may be extended through passageway 29 to provide vision within the stomach after insertion of device 20. A 6 mm. diameter articulating endoscope may be used, however the size and type of endoscope can be selected depending on the particularities associated with the procedure being performed.

Insertion device 20 further includes a second passageway 32 for passage of one or more fasteners 10. Passageway 32 preferably extends from the proximal end of housing 23, through the body portion 24, and terminates at an opening 36 near distal end portion 21. An elongate member, such as, for example, a rod 30, may be inserted into passageway 32 for advancing tissue fastener 10 through passageway 32 and into the tissue segments to be joined. Rod 30 is adapted to receive one or more fasteners 10 housed in passageway 32 and to transmit torque to fasteners 10 in order to advance fasteners 10 through passageway 32 and into the tissue segments.

Figure 7:
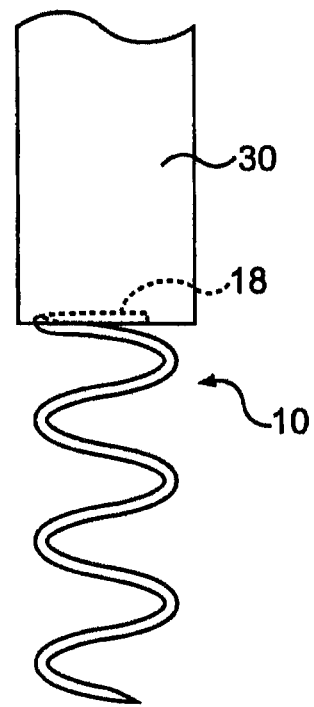
FIG. 7 is a side view of a portion of the insertion device of FIG. 5 with a tissue fastener of FIG. 2.

Referring to FIGS. 6 and 7, rod 30 preferably has a slot 34 extending radially along at least a portion of its distal end for receiving end portion 18 of fastener 10, which extends along the diameter of coil 12. The radial length of slot 34 may vary depending on the length of end portion 18 extending along the diameter coil 12. Preferably, slot 34 extends across the diameter of rod 30, as shown in FIG. 6, to allow the use of coils having end portions of varying length. The axial length of slot 34 may vary depending on the size and number of fasteners to be advanced. Slot 34 extends at least along the distal end portion of 34 and may extend up to its entire length to allow the use of multiple fasteners. The coil may be held in place with the rod in any number of manners, including, but not limited to friction, interference fit from the combination of the channel, the rod, the slot and the coil, interlocking sections between the rod and coil such as a flat spot on the coil, teeth created within the slot, a wedge shaped portion within the slot, magnets or adhesives. As well, the passageway of the insertion device may be independently designed to assist in holding the coils and rod together by manners including but not limited to friction fit, surface roughening, rifling or coating so that the coil cannot easily fall forward.

Rod 30 is rotated and advanced distally to advance fastener 10 into tissue segments. Rotation and distal advancement may be caused manually by twisting and pushing on a handle of rod 30 at its proximal end, outside of the patient. Alternatively, rotation and distal advancement may be caused by actuation of any suitable actuation mechanism attached to or integral with rod 30 at its proximal end, outside of the patient. The rod and coil may be advanced in any number of manners known in the art comprising any combination of manual, mechanical, or energy assisted means including, but not limited to, a rotary motor and worm screw arrangement, a hand trigger lever to advance and turn the rod, a plunger type arrangement including a tapped hole and worm screw, a screw driver arrangement or the like.

When rod 30 is rotated, the engagement of slot 34 with end portion 18 of coil 12 transmits torque from rod 30 to coil 12, causing coil 12 to rotate. As coil 12 advances, it exits passageway 32 and enters the tissue segments to be joined.

A plurality of fasteners can be stacked end to end in compartment or passageway 32. Multiple fasteners may be stacked one upon the other within the slot of the rod. Each fastener will release from the rod and insertion device as its proximal end exits the passageway. The slot of the rod may promote holding the fasteners until insertion is complete by means including, but not limited to, wedges or teeth along the slot, interlocking sections between the slot and coil, a slot spreader located at the end of the insertion device to release the coil, and the like. In one embodiment, the rod is withdrawn from the distal end of the insertion device after fastener insertion to receive the next coil in line for advancement.

To perform an endoscopic fundoplication procedure according to an embodiment of the present invention, device 20 is inserted through the esophagus of a patient and into the stomach. Insertion of device 20 continues until the distal end of device 20 reaches a point within the stomach below the fundus. Device 20 preferably is inserted with the side containing graspers 27,28 and arm 22 facing toward the fundus. However, it is contemplated that after insertion, device 20 can be rotated about its longitudinal axis to the desired position. Endoscope 45 may be extended through passageway 29 in device 20 to provide vision within the stomach id before, during, or after insertion of device 20. During insertion, graspers 27,28 and arm 22 remain in a closed position.

Figure 8:
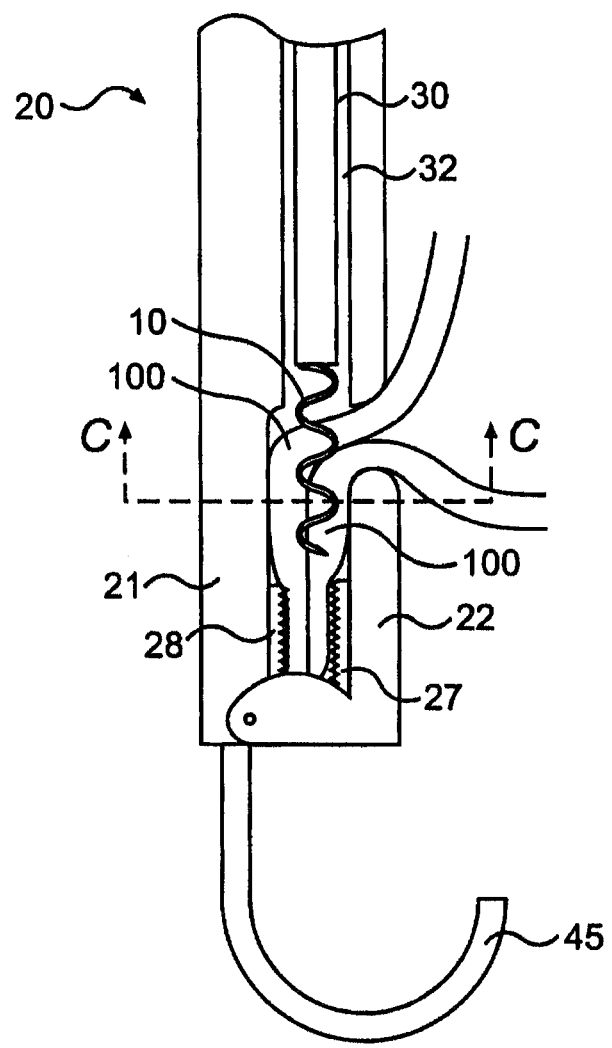
FIG. 8 is a sectional side view of the tissue fastener insertion device of FIG. 5 inserting a fastener into tissue segments.

After inserting and positioning device 20 to the desired location below the fundus, arm 22 is opened and grasper 27 is pivoted to an open position relative to grasper 28. Using a suitable visualization technique, such as articulating endoscope 45, device 20 is then lifted upward toward the opening of the esophagus in the stomach. Next, grasper 27 is closed relative to grasper 28 to grasp the gastroesophogeal junction. Arm 22 is then closed to engage the wall of the fundus and cause the fundus to fold against the side of the esophagus near its opening into the stomach, as illustrated in FIG. 8.

After the fundus wall has been folded back onto the esophagus wall, it is secured into place with a fastener 10. To do so, rod 30 and a fastener 10 are advanced through passageway 32 to opening 36 in device 20. Once tip 16 of fastener 10 reaches the tissue segments to be joined, rod 30 is rotated and advanced distally so that fastener 10 is helically wound into the tissue segments of the esophagus and stomach along the tissue juncture. In this way, fastener 10 is inserted parallel to the plane of the joined tissue segments 100.

Figure 9:
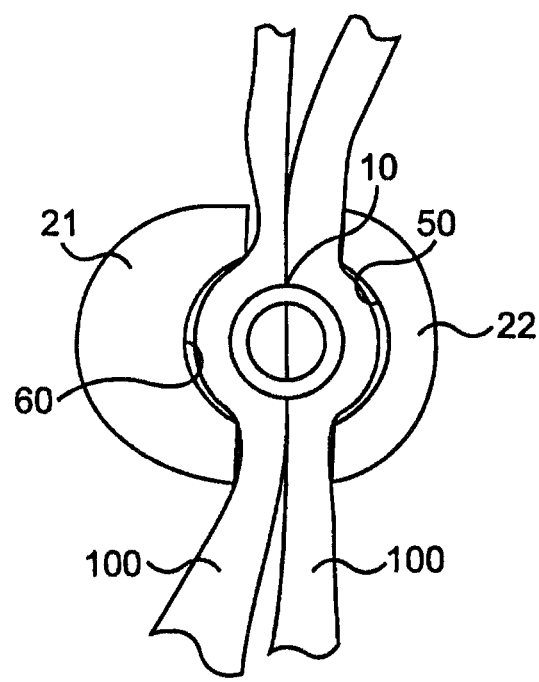
FIG. 9 is a cross-section view of the insertion device, fastener, and tissue segments shown in FIG. 8 taken along line C-C.

Device 20 may include structure to stabilize the tissue segments to be joined and aid in guidance of fastener 10 into the tissue segments. In an embodiment shown in FIG. 9, an inner surface 50 of outer arm 22 and an opposing surface 60 of distal portion 21 are contoured to aid in stabilizing the tissue segments and guiding fastener 10. The contoured surfaces preferably comprise an inwardly rounded curve slightly larger than that of coil 12 of fastener 10. While it should be recognized that either outer arm 22 or opposing portion 21 could be contoured independent of the other and still provide some guidance and stabilization, preferably both arm 22 and portion 21 are contoured to provide greater guidance and stabilization.

The above-described procedure for securing a portion of the fundus wall onto the esophagus may be repeated around the circumference of the esophagus, if desired, to deliver a plurality of fasteners 10 about that circumference.

The insertion device and fundoplication procedure just described are exemplary of a device and procedure used with the fasteners and methods to fasten tissue segments according to the present invention. It is desirable that the fastening mechanisms and/or methods according to the present invention can be installed or performed relatively quickly in a relatively non-invasive manner, and can create a substantially uniform fold of tissue once installed. Although the fasteners and methods according to the present invention are especially suitable for use in an endoscopic fundoplication procedure, those in the medical arts will understand that the fasteners and methods may be suitable for other endoscopic and nonendoscopic surgical applications requiring the fastening of tissue segments.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for fastening tissue, comprising:
   a coil disposed along a longitudinal axis of the device, the coil configured to advance in a distal direction and having a sharp distal end to penetrate tissue; and
   a first arm and a second arm disposed about the coil for receiving tissue therebetween, wherein the first arm is stationary along an axis parallel to the longitudinal axis of the device as the second arm pivots relative to the first arm.

2. The device of claim 1, wherein the device comprises a first channel and a second channel, the second channel including the coil.

3. The device of claim 2, wherein the first channel extends through the first arm.

4. The device of claim 1, wherein the coil has a variable pitch and is configured to be helically wound into the tissue.

5. The device of claim 1, wherein the coil is configured to rotate relative to the first arm and the second arm.

6. The device of claim 1, configured for insertion into the esophagus.

7. The device of claim 1, wherein the second arm has an extended position and a retracted position, the second arm being positioned at an angle relative to the longitudinal axis in the extended position and positioned substantially along the longitudinal axis in the retracted position.

8. The device of claim 7, wherein the device is configured to hold the tissue when the second arm is in the retracted position.

9. The device of claim 1, wherein the device is configured to hold folded tissue.

10. The device of claim 1, wherein a proximal end of the coil lies along a diameter of the coil.

11. The device of claim 1, wherein the coil comprises at least one of stainless steel, Nitinol, or titanium.

12. The device of claim 1, coupled to an imaging device for viewing the distal end of the coil.

13. A device for fastening tissue, comprising:
    a shaft defining a plurality of channels therethrough;
    a coil disposed along a longitudinal axis of the device, the coil configured to advance in a distal direction and having a sharp distal end; and
    a first arm and a second arm disposed proximate a distal end of the shaft and about the coil for receiving a tissue fold therebetween, wherein a first channel of the plurality of channels extends from the shaft through the first arm, and the second arm pivots about a distal surface of the device from a first position at an angle relative to the longitudinal axis to a second position substantially aligned with the longitudinal axis.

14. The device of claim 13, wherein the plurality of channels comprises a second channel that includes the coil.

15. The device of claim 14, wherein at least one of the first channel and the second channel extends from a proximal end of the device to the distal surface of the device.

16. The device of claim 13, further comprising an imaging device configured to view the distal end of the coil.

17. The device of claim 16, wherein the second arm pivots adjacent to the imaging device.

18. A device for fastening tissue, comprising:
a coil disposed along a longitudinal axis of the device, the coil configured to advance in a distal direction and having a sharp distal end to penetrate tissue; and
at least two arms including a first arm and a second arm disposed adjacent to the coil for receiving tissue therebetween, wherein the first arm is stationary along an axis parallel to the longitudinal axis of the device, and the second arm pivots with respect to the first arm.

19. The device of claim 18, wherein the device comprises a first channel extending through the first arm and a second channel including the coil.

20. The device of claim 18, wherein at least one of the arms includes teeth for grasping the tissue.

* * * * *